US00PP36312P2

(12) United States Plant Patent
van Dijk

(10) Patent No.: US PP36,312 P2
(45) Date of Patent: Dec. 10, 2024

(54) ***ANTHURIUM* PLANT NAMED 'AN2704879'**

(50) Latin Name: *Anthurium andreanum*
Varietal Denomination: AN2704879

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/610,211

(22) Filed: Mar. 19, 2024

(51) Int. Cl.
*A01H 5/02* (2018.01)
*A01H 6/00* (2018.01)

(52) U.S. Cl.
USPC ..... Plt./365

(58) Field of Classification Search
CPC ..... A01H 5/02; A01H 5/00; A01H 6/00
See application file for complete search history.

(56) References Cited

U.S. PATENT DOCUMENTS

PP34,252 P2 * 5/2022 Van Dijk ..... A01H 6/00
Plt./365

OTHER PUBLICATIONS

CPVO Register Version 4.20.1 retrieved on Jul. 9, 2024 at https://online.plantvarieties.eu/publicConsultation Details?registerId=20222634&denomination=an2704879, 2 pp. (Year: 2024).*

UPOV Pluto Jul. 9, 2024 retrieved on Jul. 9, 2024 at https://plluto.upov.int/result, one page. (Year: 2024).*

* cited by examiner

*Primary Examiner* — June Hwu

(74) *Attorney, Agent, or Firm* — C. Anne Whealy

(57) ABSTRACT

A new and distinct cultivar of *Anthurium* plant named 'AN2704879', characterized by its upright to outwardly arching and uniform plant habit; freely clumping growth habit; bushy and dense plants; narrowly cordate to close to sagittate dark green-colored leaves; freely flowering habit; inflorescences that are positioned within to slightly above the foliar plane on strong and erect scapes; broadly cordate white and red bi-colored spathes and red purple and red-colored spadices; and durable spathes that impart good inflorescence longevity.

2 Drawing Sheets

Figure 1:
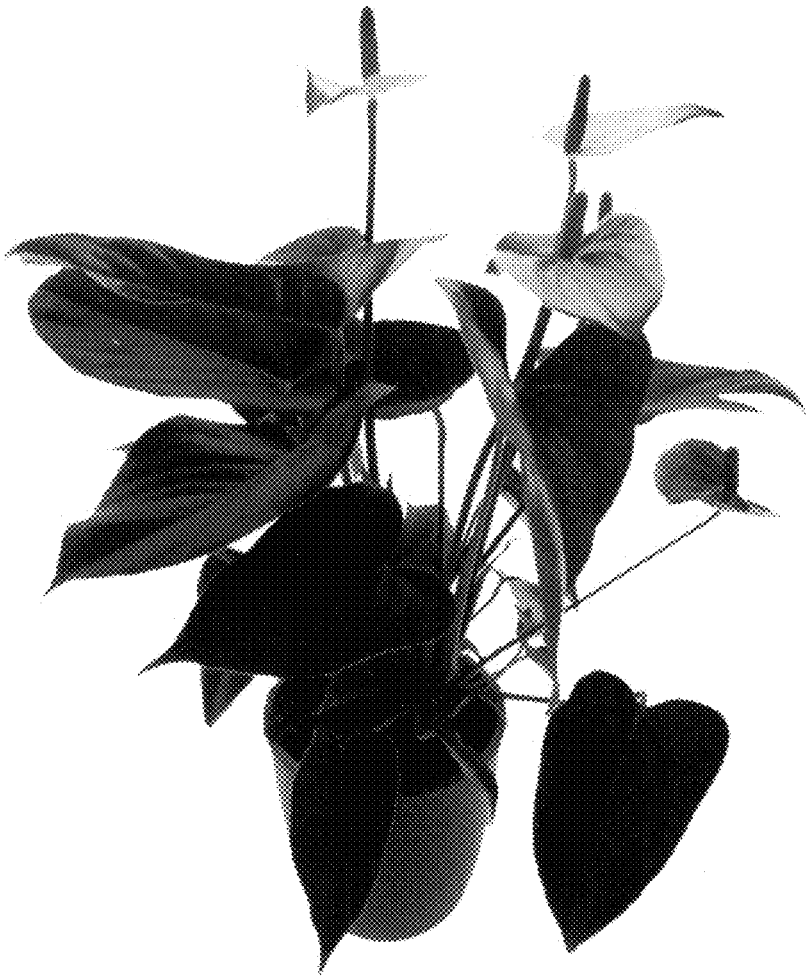

Botanical designation: *Anthurium andreanum.*
Cultivar denomination: 'AN2704879'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Anthura B. V. of Bleiswijk, The Netherlands on Nov. 22, 2022, application number 2022/2634. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Anthurium* plant, botanically known as *Anthurium andreanum* and hereinafter referred to by the name 'AN2704879'.

The new *Anthurium* plant is a product of a controlled breeding program conducted by the Inventor in Bleiswijk, The Netherlands. The objective of the breeding program is to create new freely-clumping *Anthurium* plants with attractive bi-colored, durable and glossy spathes.

The new *Anthurium* plant originated from a cross-pollination made by the Inventor in May 2012 in Bleiswijk, The Netherlands of a proprietary selection of *Anthurium andreanum* identified as code number 07-018781-0008, not patented, as the female, or seed, parent with a proprietary selection of *Anthurium andreanum* identified as code number 09-022746-0004, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in August 2014.

Asexual reproduction of the new *Anthurium* plant by in vitro meristem propagation in a controlled environment in Bleiswijk, The Netherlands since June 2016 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2704879'. These characteristics in combination distinguish 'AN2704879' as a new and distinct *Anthurium* plant:

1. Upright to outwardly arching and uniform plant habit.
2. Freely clumping growth habit; bushy and dense plants.
3. Narrowly cordate to close to sagittate dark green-colored leaves.
4. Freely flowering habit.
5. Inflorescences that are positioned within to slightly above the foliar plane on strong and erect scapes.
6. Broadly cordate white and red bi-colored spathes and red purple and red-colored spadices.
7. Durable spathes that impart good inflorescence longevity.

Plants of the new *Anthurium* differ primarily from plants of the female parent selection in the following characteristics:

1. Spathe apices of plants of the new *Anthurium* are abruptly acute whereas spathe apices of plants of the female parent selection are broadly acuminate.
2. Spadices of plants of the new *Anthurium* are not as tapering as spadices of plants of the female parent selection.

Plants of the new *Anthurium* differ primarily from plants of the male parent selection in the following characteristics:

1. Leaves of plants of the new *Anthurium* are narrowly cordate to close to sagittate in shape whereas leaves of plants of the male parent selection are narrowly ovate in shape.
2. Spathes of plants of the new *Anthurium* are smaller than spathes of plants of the male parent selection.

Plants of the new *Anthurium* can also be compared to plants of *Anthurium andreanum* 'AN2608442', disclosed in U.S. Plant Pat. No. 34,252. In side-by-side comparisons, plants of the new *Anthurium* differ primarily from plants of 'AN2608442' in the following characteristics:

1. Plants of the new *Anthurium* are larger than plants of 'AN2608442'.
2. Spathes of plants of the new *Anthurium* are white and red bi-colored whereas spathes of plants of 'AN2608442' are white and pink bi-colored.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2704879' grown in a container.

Figure 2:
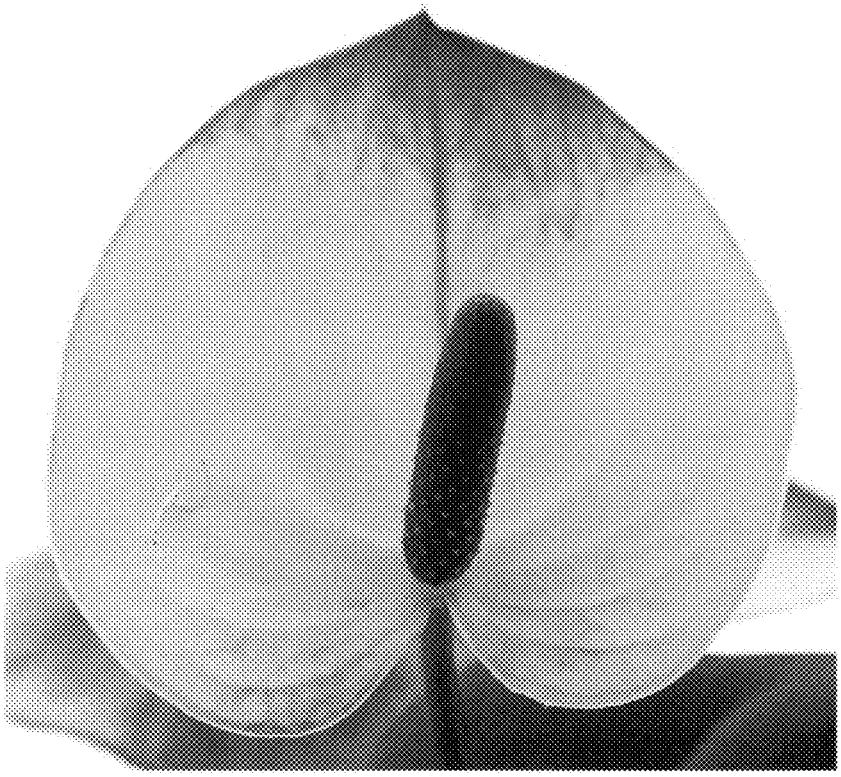

The photograph on the second sheet (FIG. 2) is a close-up view of a typical inflorescence of 'AN2704879'.

DETAILED BOTANICAL DESCRIPTION

The aforementioned photographs and following observations and measurements describe plants grown in 14-cm containers in Bleiswijk, The Netherlands during the autumn in a glass-covered greenhouse. Plants were grown under conditions and practices which approximate those generally used in commercial *Anthurium* production. During the production of the plants, day and night temperatures ranged from about 19° C. to 22.5° C. and light levels ranged from 100 μmol to 200 μmol. Plants were eleven months old when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2704879'.

Parentage:

*Female, or seed, parent.*—Proprietary selection of *Anthurium andreanum* identified as code number 07-018781-0008, not patented.

*Male, or pollen, parent.*—Proprietary selection of *Anthurium andreanum* identified as code number 09-022746-0004, not patented.

Propagation:

*Type.*—By in vitro meristem propagation.

*Time to initiate roots, summer and winter.*—About two weeks at temperatures about 19° C. to 22.5° C.

*Time to produce a rooted young plant, summer and winter.*—About six to eight weeks at temperatures about 19° C. to 22.5° C.

*Root description.*—Medium in thickness, fibrous; typically creamy white in color, actual color of the roots is dependent on substrate composition, water quality, fertilizer type and formulation, substrate temperature and physiological age of roots.

*Rooting habit.*—Freely branching, medium density.

Plant description:

*Plant shape.*—Upright to outwardly spreading and uniform plant habit; overall shape, close to globular.

*Growth habit.*—Freely clumping habit with about six clumps per plant imparting a bushy and dense appearance; moderately vigorous growth habit and moderate growth rate.

*Plant height, from soil level to top of leaf plane.*—About 29.2 cm.

*Plant height, from soil level to top of inflorescences.*—About 40.1 cm.

*Plant diameter or spread.*—About 46 cm.

Leaf description:

*Arrangement.*—Alternate; simple; about 2.5 leaves per clump.

*Length.*—About 22.5 cm.

*Width.*—About 11.7 cm.

*Shape.*—Narrowly cordate to close to sagittate; slightly to moderately carinate.

*Apex.*—Apiculate with mucronate tip; tip points downwardly.

*Base.*—Deeply cordate to shallow auriculate.

*Margin.*—Entire; slightly and coarsely undulate.

*Texture and luster, upper and lower surfaces.*—Smooth, glabrous; moderately leathery to leathery; glossy.

*Venation pattern.*—Pinnate.

*Color.*—Developing leaves, upper surface: Close to 146A; narrow marginal edges, close to 197A; towards the apex, close to 178B and 178C. Developing leaves, lower surface: Close to 146B; narrow marginal edges, close to a blend of 152B and 199B;

towards the apex, close to 178B and 178C. Fully expanded leaves, upper surface: Slightly darker than a blend of NN137A and 147A; narrow marginal edges, close to 144A; towards the apex, close to 178B and 178C; venation, close to 143B. Fully expanded leaves, lower surface: Close to 146B; narrow marginal edges, close to 145A; towards the apex, close to 197A; venation, close to 151D.

*Petioles*.—Length: About 18.4 cm. Diameter: Distally, about 4.5 mm; proximally, about 6 mm. Strength: Strong. Texture and luster, upper and lower surfaces: Smooth, glabrous; glossy. Color, upper surface: Close to 146A, densely covered with fine dots, close to 144B. Color, lower surface: Close to 146A tinged with close to 152A, and densely covered with fine dots, close to 144B. Geniculum length: About 2 cm. Geniculum diameter: About 5.5 mm. Geniculum texture and luster, upper and lower surfaces: Smooth, glabrous; glossy. Geniculum color, upper surface: Close to 146A, densely covered with fine dots, close to 144B. Geniculum color, lower surface: Close to 146A and 146B, densely covered with fine dots, close to 144B. Wing length: About 2.6 cm. Wing diameter: About 5 mm. Wing color: Close to 145A tinged with close to 166B.

Inflorescence description:

*Inflorescence arrangement and flowering habit*.—Spathes with spadices held within and slightly above the foliar plane on strong and erect scapes; flowering structures arise from leaf axils; freely and continuous flowering year-round in controlled temperature greenhouses in The Netherlands; typically about seven developing and developed inflorescences per plant at one time; inflorescence development commences about 2.5 to 3.5 months after planting.

*Inflorescence longevity*.—Spathes maintain good substance for about two months on the plant; inflorescences persistent.

*Fragrance*.—None detected.

*Spathes*.—Length: About 10 cm. Width: About 8.9 cm. Shape: Broadly cordate; slightly convex to slightly concave. Apex: Abruptly acute with a mucronate tip. Base: Cordate. Margin: Entire; slightly and coarsely undulate. Aspect: At about 90° to about −20° from the peduncle axis. Texture and luster, upper and lower surfaces: Smooth, glabrous; moderately leathery; glossy. Color: When developing, front surface: Close to 36D; towards the base, tinged with close to 157A; towards the apex, close to 47A; main vein, margins and tip, close to N45A and N45B. When developing, rear surface: Close to 155D; towards the base, tinged with close to 145C, 145D and 150D; venation and margins, close to N45B to N45D. Fully developed, front surface: Close to 155A and 155B; towards the base, slightly tinged with close to 157D with venation, close to 145B and 145C; towards the apex, close to 47B and 47C; main vein, close to 46C; margins and tip, close to 46A and 185A; with subsequent development, color becoming closer to 144A and towards the apex, close to 145B; main vein, close to 47A surrounded by 47C, and lateral venation, close to 141B and 143A; distal margins and tip, closer to 46A. Fully developed, rear surface: Close to 155C; towards the base, tinged with close to 145D and 150D with venation, close to 144A and 144B; towards the apex, close to 49C; main vein and distal venation, close to 47A; margins and tip, close to 46A; with subsequent development, color becoming closer to 144A; distal margins, close to 184A and 184B, and venation, close to 177A to 177D.

*Spadices*.—Length: About 4.1 cm. Diameter: About 1.1 cm. Shape: Columnar, slightly tapering towards the apex; apex, obtuse; base, obtuse; in cross-section, rounded. Aspect: About 70° from the spathe axis and about 15° from the peduncle axis. Color: Immature: Close to 51A and 53D and distally, close to 48A and 50B. Mature: Close to 51A and distally, close to 60A. Flowers: Type: Hermaphroditic. Quantity per spadix: Numerous, about 160. Height: Less than 0.5 mm. Diameter: About 2.5 mm. Shape: Roughly square. Anther color: Close to 51B. Pollen amount: None observed. Stigma color: Close to 51D.

*Scape*.—Length: About 28.8 cm. Diameter: About 4.5 mm. Strength: Strong. Aspect: About 25° from vertical. Color: Close to 144A and distally, close to 144B.

*Seed and fruit*.—To date, seed and fruit development has not been observed on plants of the new *Anthurium*.

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures about 30° C. and to be hardy to USDA Hardiness Zone 10.

It is claimed:

1. A new and distinct *Anthurium* plant named 'AN2704879' as herein illustrated and described.

* * * * *